(12) United States Patent
Stojanov

(10) Patent No.: US 8,859,283 B2
(45) Date of Patent: Oct. 14, 2014

(54) CRYOPRESERVATION OF BIOLOGICAL CELLS AND TISSUES

(75) Inventor: Tomas Stojanov, Sydney (AU)

(73) Assignee: Genea Limited, Sydney (AU)

( * ) Notice: Subject to any disclaimer, the term of this patent is extended or adjusted under 35 U.S.C. 154(b) by 533 days.

(21) Appl. No.: 12/919,071

(22) PCT Filed: Feb. 25, 2009

(86) PCT No.: PCT/AU2009/000212
§ 371 (c)(1),
(2), (4) Date: Aug. 24, 2010

(87) PCT Pub. No.: WO2009/105813
PCT Pub. Date: Sep. 3, 2009

(65) Prior Publication Data
US 2010/0317108 A1 Dec. 16, 2010

(30) Foreign Application Priority Data
Feb. 25, 2008 (AU) ................. 2008900890

(51) Int. Cl.
| | | |
|---|---|---|
| *A01N 1/00* | (2006.01) | |
| *A01N 1/02* | (2006.01) | |
| *C12N 5/02* | (2006.01) | |
| *C12M 1/00* | (2006.01) | |
| *B01L 3/00* | (2006.01) | |
| *B01L 7/00* | (2006.01) | |
| *G01N 1/42* | (2006.01) | |

(52) U.S. Cl.
CPC ........... *A01N 1/02* (2013.01); *B01L 2300/1805* (2013.01); *B01L 2300/0681* (2013.01); *G01N 1/42* (2013.01); *B01L 2300/1844* (2013.01); *B01L 3/508* (2013.01); *B01L 7/50* (2013.01)
USPC ........................................ 435/374; 435/307.1

(58) Field of Classification Search
CPC ......... A01N 1/02; A01N 1/00; A01N 1/0221; A01N 1/0242; A01N 1/0268; B01L 2300/0681
USPC ............................ 435/374, 307.1; 424/93.7
See application file for complete search history.

(56) References Cited

U.S. PATENT DOCUMENTS

| | | |
|---|---|---|
| 5,026,342 A | 6/1991 | Hammerstedt et al. |
| 5,261,870 A | 11/1993 | Hammerstedt et al. |
| 5,894,733 A | 4/1999 | Brodner |
| 6,176,089 B1 | 1/2001 | Bouche |
| 2004/0259072 A1 | 12/2004 | Kuwayama et al. |
| 2006/0188865 A1 | 8/2006 | Fuhr |

FOREIGN PATENT DOCUMENTS

WO 99/08513 A1 2/1999

OTHER PUBLICATIONS

Cryocane. www.coleparmer.com/buy/product/52491-thermo-scientific-nalgene-cryocane-aluminum-300-ml-holds-6-vials-5015-0002.html#Specs; downloaded on Nov. 13, 2012, p. 1.*
Abe et al, "Feasibility of a Nylon-Mesh Holder for Vitrification of Bovine Germinal Vesicle Oocytes in Subsequent Production of Viable Blastocysts," Biology of Reproduction, 72, 1416-1420, 2005.
Matsumoto et al, "Vitrification of Large Quantities of Immature Bovine Oocytes Using Nylon Mesh," Cryobiology, 42, 139-144, 2001.
Park et al, "Simple, Efficient and Successful Vitrification of Bovine Blastocysts Using Electron Microscope Grids," Human Reproduction, vol. 14, No. 11, 2838-2843, 1999.
Park et al, "Ultra-Rapid Freezing of Human Multipronuclear Zygotes Using Electron Microscope Grids," Human Reproduction, vol. 15, No. 8, 1787-1790, 2000.
Dinnyes et al, "High Developmental Rates of Vitrified Bovine Oocytes Following Parthenogenetic Activation, In Vitro Fertilization, and Somatic Cell Nuclear Transfer," Biology of Reproduction, 63, 513-518, 2000.

* cited by examiner

Primary Examiner — Taeyoon Kim
(74) Attorney, Agent, or Firm — Richard M. Goldberg

(57) ABSTRACT

The method involves placing an oocyte cell in a cell holder (1), securing the cell holder in a treatment station, applying a treatment solution to the cell by washing the cell with the solution, and rapidly cooling the cell holder and cell to a predetermined cryopreservation temperature for cryopreservation of the cell. The cell is cooled at a high rate sufficient to permit vitrification of the cell and any surrounding treatment solution to occur. The cell is then maintained at or below a predetermined storage temperature for storage. The method allows multiple cells to be treated simultaneously each secured within a respective cell holder.

6 Claims, 8 Drawing Sheets

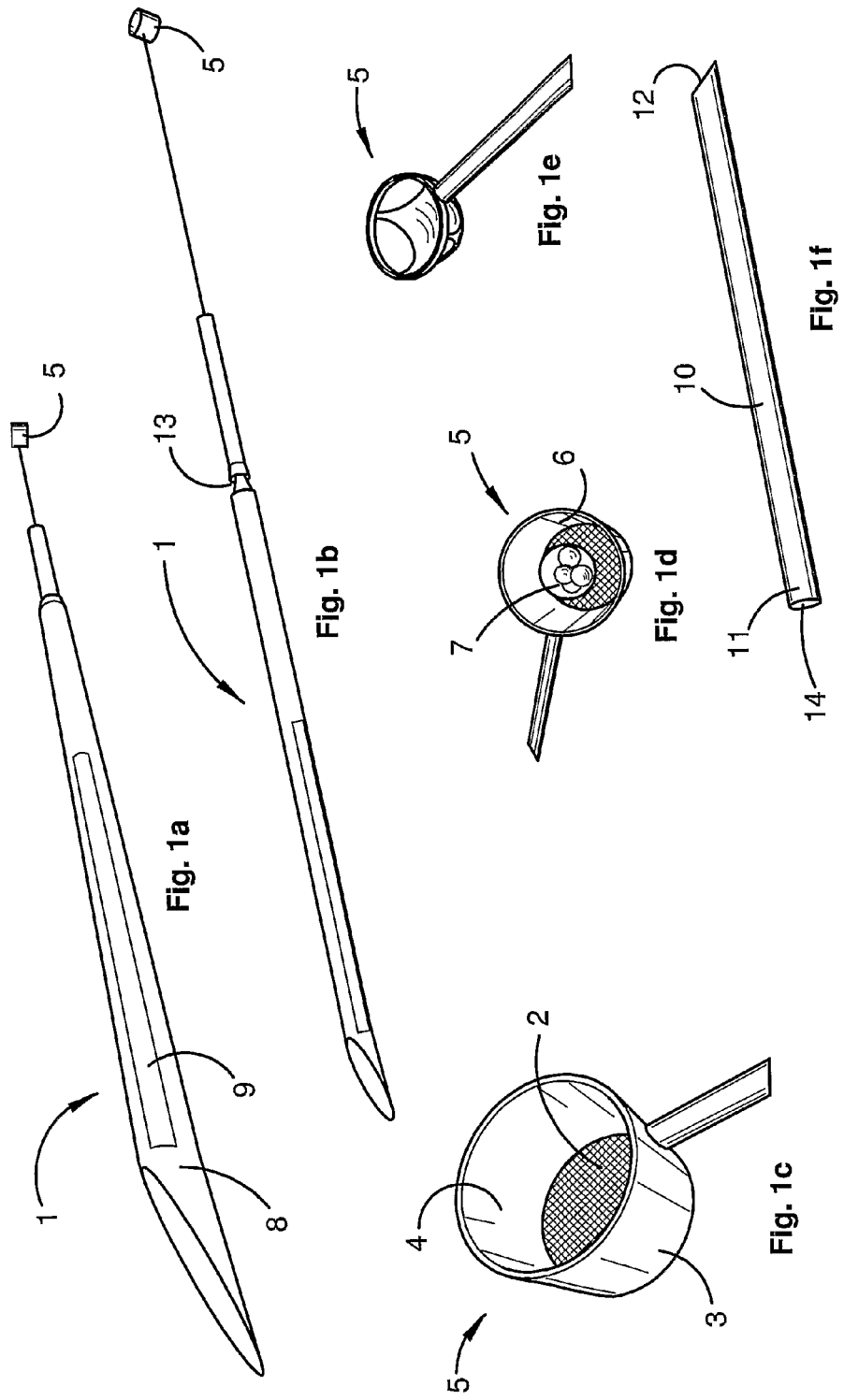

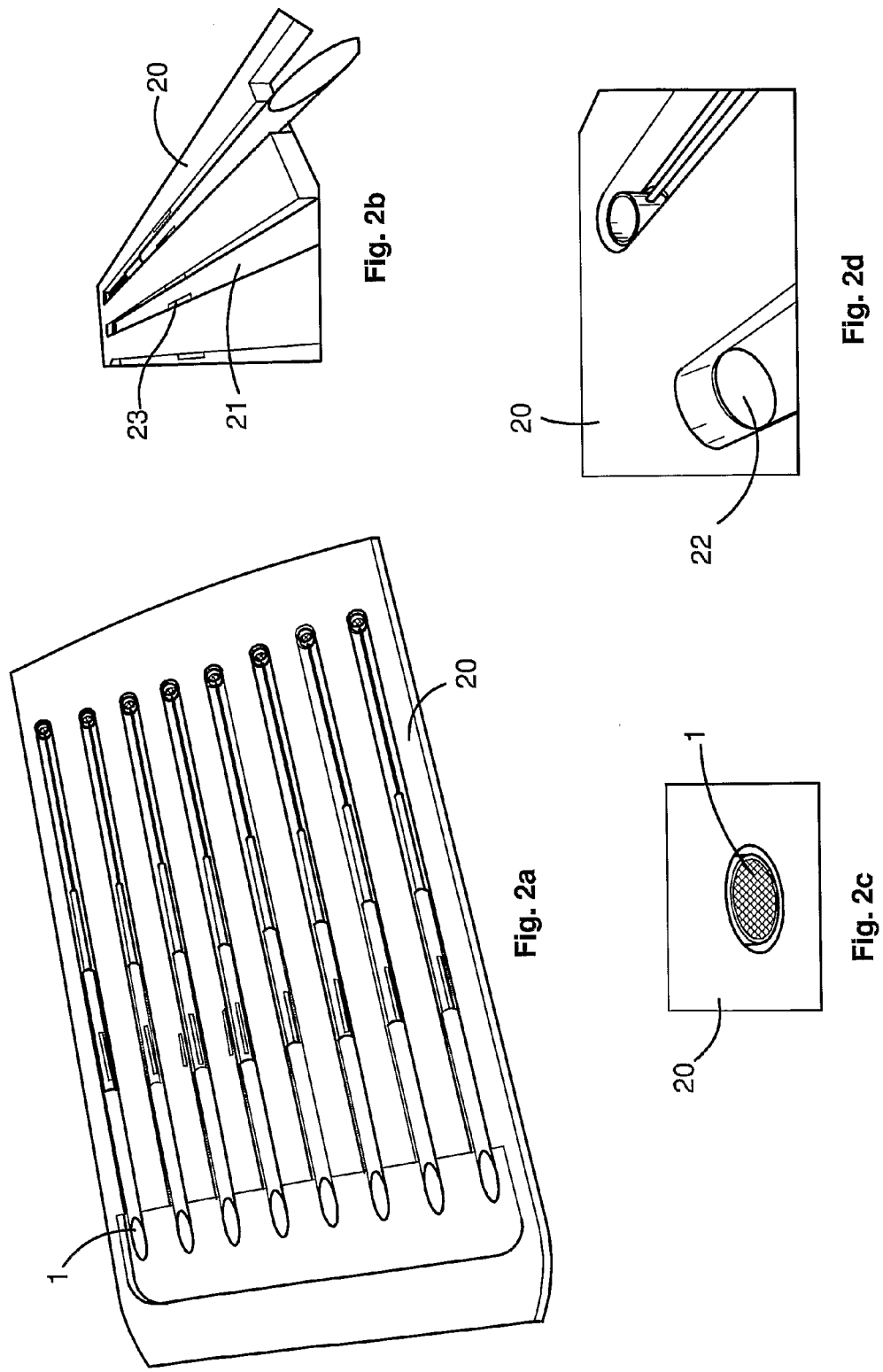

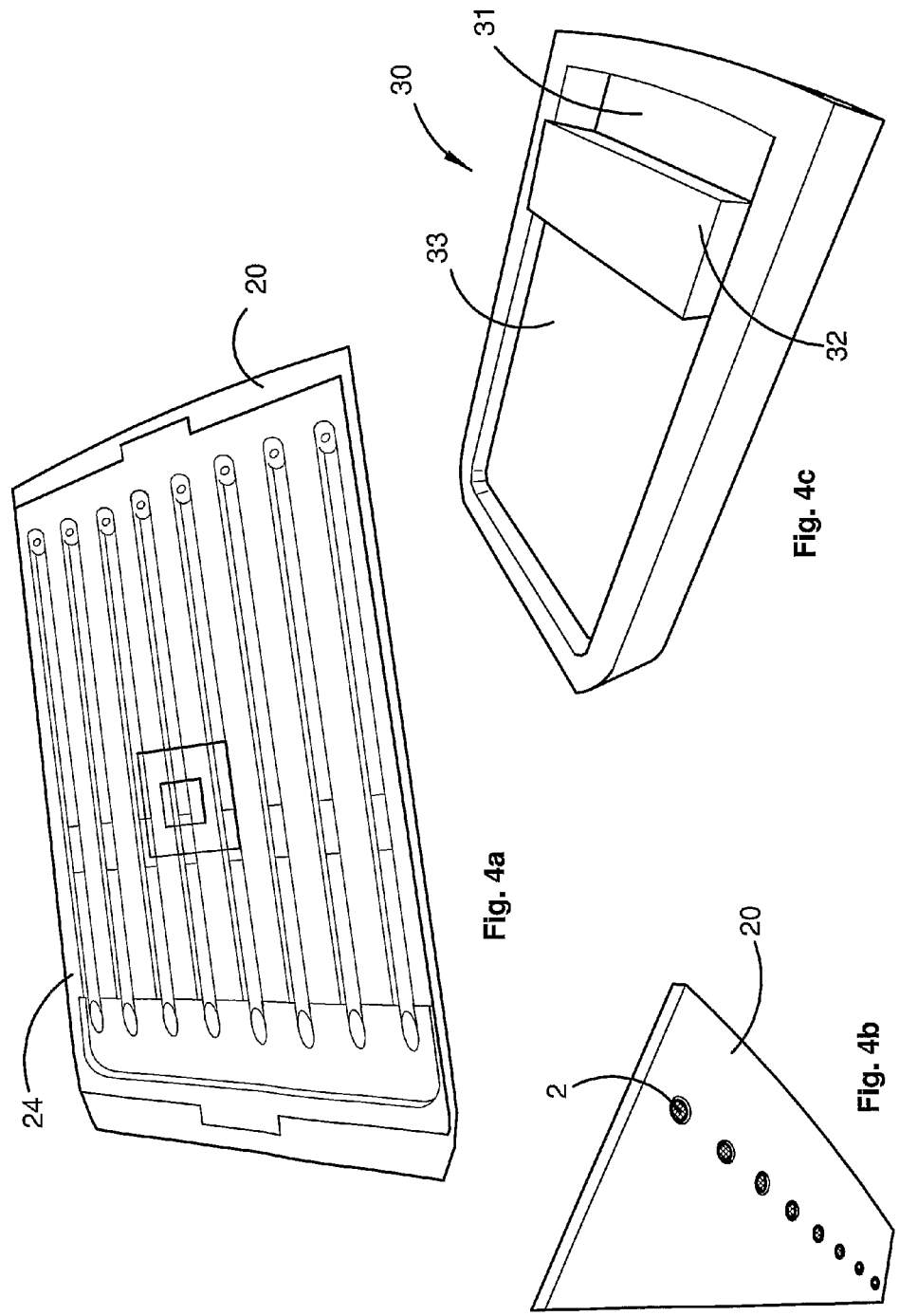

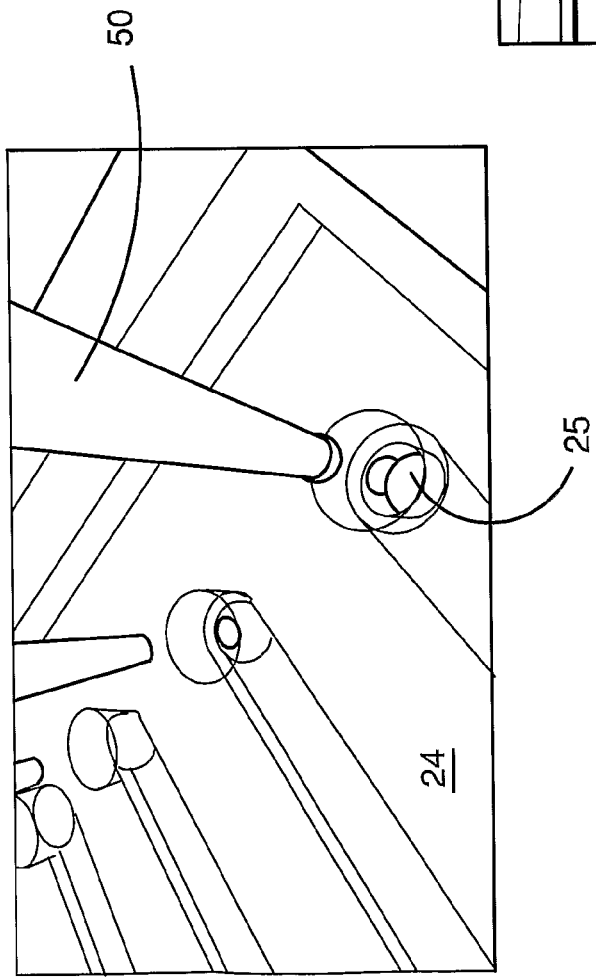
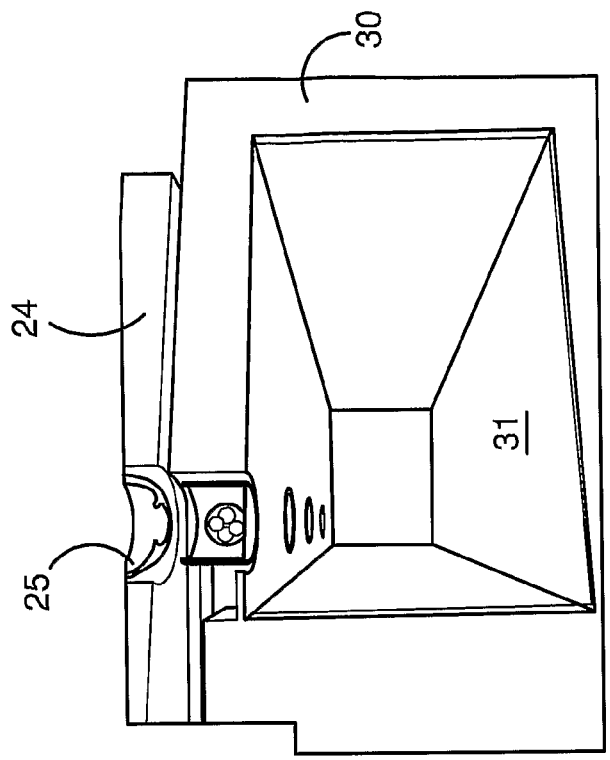
Fig. 5a
Fig. 5b

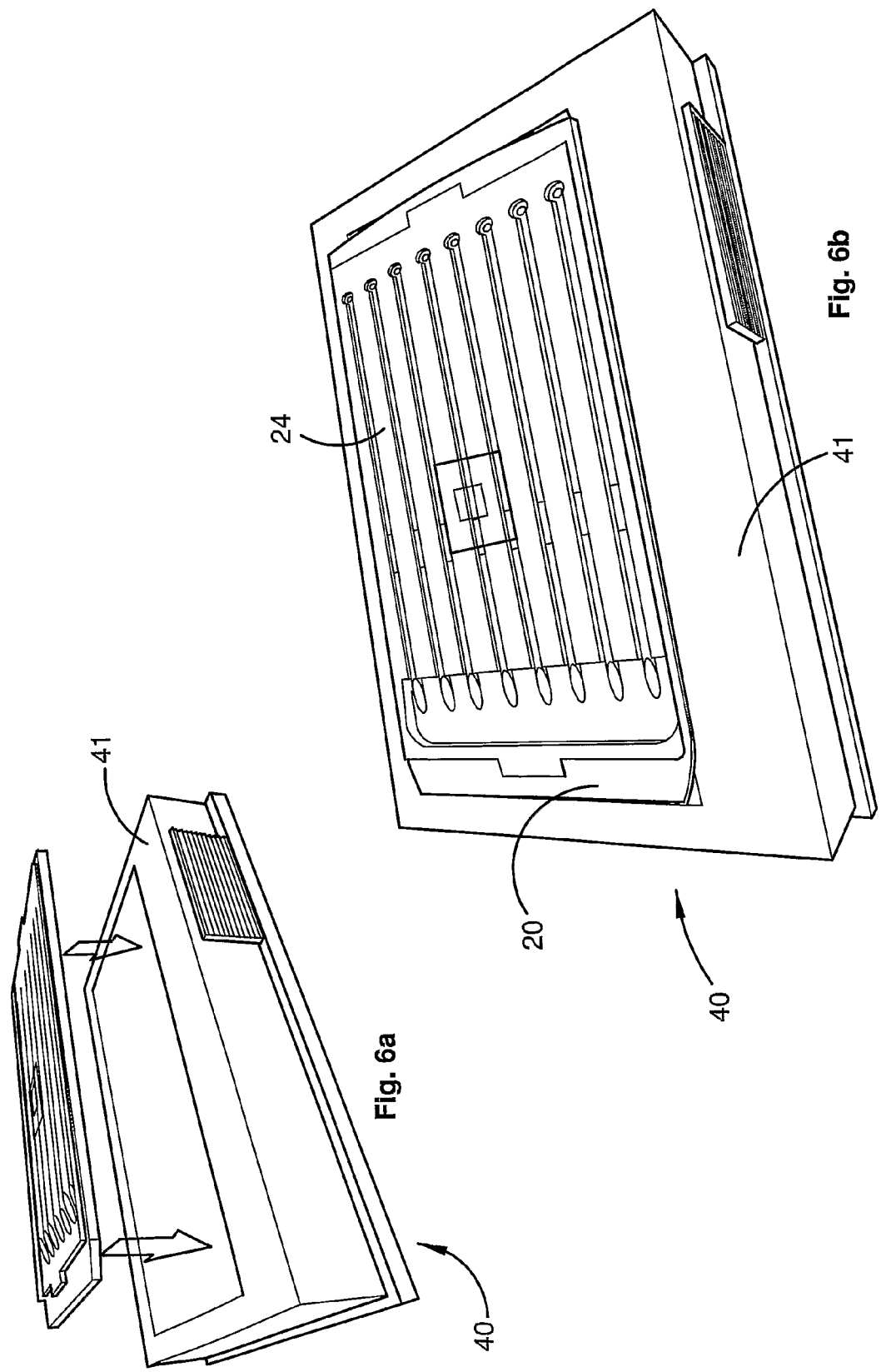

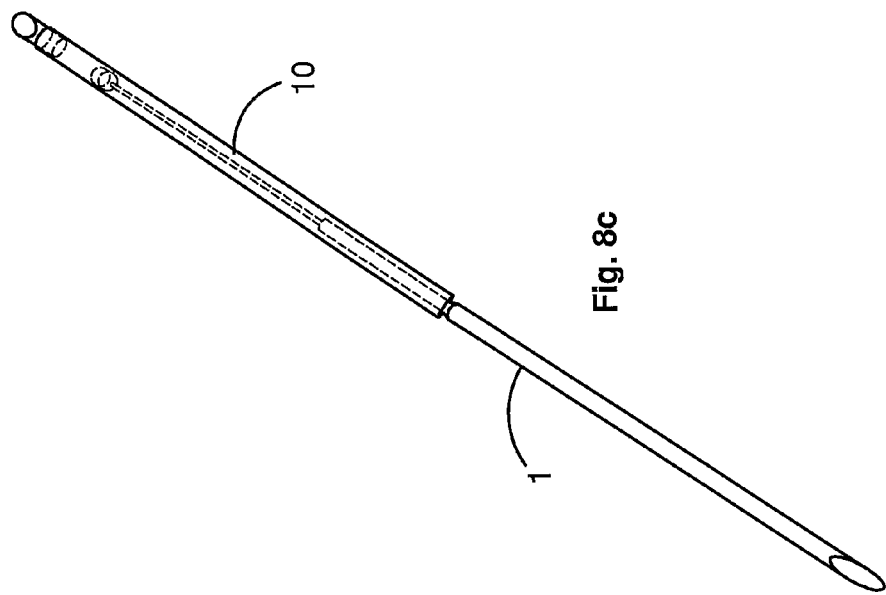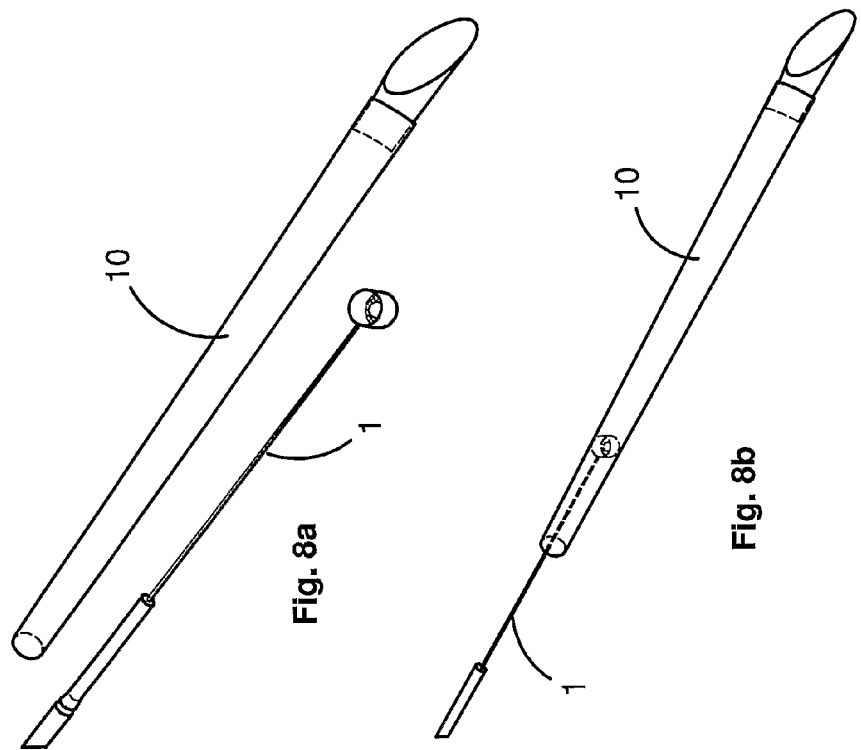

CRYOPRESERVATION OF BIOLOGICAL CELLS AND TISSUES

FIELD OF THE INVENTION

The present invention relates generally to a method and apparatus for the cryopreservation of biological cells and tissues.

The invention has been developed primarily for use in the cryopreservation of human oocytes, embryos and stem cells by vitrification as applied during In-Vitro Fertilisation (IVF) procedures. It will be appreciated, however, that the invention is not limited to to this particular method of cryopreservation, and may also be used in connection with cryopreservation of human and non-human oocytes, embryos and stem cells or other biological tissues and cells.

BACKGROUND OF THE INVENTION

The following discussion of the prior art is provided as technical background, to enable the features and benefits of the invention to be fully appreciated in an appropriate technical context. However, any reference to the prior art should not be taken as an express or implied admission that such art is widely known or forms part of common general knowledge in the field.

The technology for cryopreserving human and animal embryos as well as many other types of biological cells and small tissue samples is known.

In particular, during In-Vitro Fertilisation (IVF) procedures, embryo cryopreservation involves the extraction, fertilization, freezing and storing of embryos. As required, the embryos can be thawed and transferred to the uterus for normal development.

More recently, similar cryopreservation techniques have been applied to unfertilized eggs or oocytes. Oocyte cryopreservation involves the extraction, freezing and storing of the female eggs, or oocytes in an unfertilized state. As required, the eggs can be thawed, fertilized, and transferred to the uterus as embryos. The technique of freezing oocytes rather than embryos is considered desirable for medical, personal and ethical reasons.

Currently there are two known methods for cryopreserving biological cells and tissues. In order to succeed, all cryopreservation strategies, must avoid ice crystal formation, solution effects, and osmotic shock. The traditional method is to slowly cool the cell/s and its surrounding solution to the storage temperature and purposely initiate the formation of ice crystals remote from the cell/s. A more recent method known as vitrification, transforms the solution into a glasslike amorphous solid that is free from any crystalline structure, following extremely rapid cooling.

In both methods, it is known to use additional chemicals to avoid cell damage. These chemicals are known as cryoprotectants and may be divided into two categories, permeating and nonpermeating.

Permeating cryoprotectants are small molecules that readily permeate the membranes of cells. They form hydrogen bonds with water molecules and prevent ice crystallization. Some examples are ethylene glycol (EG), dimethyl sulphoxide (DMSO) and glycerol. At low concentrations in water, they lower the freezing temperature of the resulting mixture. However, at high enough concentrations, they inhibit the formation of the characteristic ice crystal and lead to the development of a solid, glasslike, or vitrified state in which water is solidified, but not crystalline or expanded. The toxicity at this concentration is quite high and therefore the cell can be exposed to this solution either for a very short period of time (as with vitrification techniques) or at very low temperatures, at which the metabolic rate of the cell is very low.

In contrast to the permeating cryoprotectants, nonpermeating cryoprotectants remain extracellular. Some examples are the disaccharides trehalose and sucrose. They act by drawing free water from within the cell, thus dehydrating the intracellular space. As a result, when they are used in combination with a permeating cryoprotectant, the net concentration of the permeating cryoprotectant can be increased in the intracellular space. This further assists the permeating cryoprotectant in preventing ice-crystal formation.

During vitrification, permeating cryoprotectants may be added at a high concentration while the cell's temperature is controlled at a predetermined level above freezing. However, because the toxicity of this high concentration of permeating cryoprotectant is substantial, the cell/s cannot be kept at these temperatures for long. Instead, a very short time is allowed for equilibration, after which the embryos/oocytes are plunged directly into liquid nitrogen. This extremely rapid rate of cooling not only minimizes the negative effects of the cryoprotectant on the cell, but also further protects against ice-crystal formation by encouraging vitrification.

A typical vitrification process involves exposing the cell to three or more vitrification solutions. The vitrification solutions are added to respective wells in a multi-well culture dish. The dish and solutions are warmed to predetermined temperature selected depending on the type of cell or tissue.

In a typical protocol, the cell is transferred to a first solution in a first well and washed by carefully moving the cell through the solution with a cell pipetting device. The washing process is repeated in the second, third and fourth wells for various predetermined periods of time, until the cell is ready for cryopreservation.

The cell is then drawn up with a predetermined measure of vitrification solution with a pipettor. A droplet containing the cell to be vitrified is wiped onto the hook of a fiber plug.

The fiber plug may be transferred directly into liquid nitrogen or on to the surface of a vitrification block that has been pre-cooled with liquid nitrogen. The fiber plug is placed onto the surface of the block for a minimum period during which time the cell and fluid become vitrified. The fiber plug is then inserted into a pre-chilled straw or other device located in a slot in the vitrification block before being transferred to long-term cold storage in either liquid nitrogen or liquid nitrogen vapour.

To maximize the survival chances of the cell it is very important that the process is carried out with minimal manipulation. In addition, the process and timing of washing and cooling must be adhered to with minimal variation. The process is both time consuming and requires the technician to have a relatively high level of training and skill to achieve an acceptable survival ratio.

It is an object of the present invention to overcome or substantially ameliorate one or more of the limitations of the prior art, or at least to provide a useful alternative.

DISCLOSURE OF THE INVENTION

In a first aspect, the invention provides a method for the cryopreservation of an organic cell, said method including the steps of:
    providing an organic cell for cryopreservation;
    holding the cell in a cell holder;
    securing the cell holder containing the cell at a treatment station;

applying first treatment solution to the cell;
cooling said cell holder and cell to a predetermined cryopreservation temperature; and
maintaining the cell at or below a storage temperature.

The term "biological cell" as used herein is intended to apply to any small biological cell or groups of cells whether bound or unbound. It is intended to include single cells such as oocytes and stem cells, small multi-cell structures such as embryos and small tissue samples. Preferably, said cell is cooled at a cooling rate sufficient to promote vitrification of the cell and surrounding treatment solution.

Preferably, said step of applying a treatment solution includes retaining said cell in said cell holder and allowing said solution to flow over said cell.

Preferably, the cell holder includes filtration means allowing fluid to pass through the filtration means whilst retaining the cell.

Preferably, the cell holder includes sidewalls thereby forming a cup-shaped holding vessel and defining an open inlet. Preferably, said step of washing said cell includes retaining said cell in said cell holder and allowing said solution to flow over said cell.

Preferably, the retaining means includes a filter.

Preferably, the cell holder includes sidewalls thereby forming a cup-shaped holding vessel defining an open top inlet.

Preferably, the step of washing said cell includes sequentially showering said cell with first and second treatment solutions.

Preferably, said step of washing said cell includes sequentially showering said cell with a plurality of treatment solutions.

Preferably, after said washing step, the method includes the step of transferring the cell holder to a cooling station prior to cooling said cell.

Preferably, a plurality of said cell holders are secured in an array and washed simultaneously at the treatment station.

Preferably, said cell holder is secured in a cell holder frame in the form of a tray.

Preferably, said tray is secured to said treatment station.

Preferably, said tray includes a plurality of engagement formations for engaging said cell holder thereby securing a plurality of corresponding cell holders to the frame in an array.

In a second aspect the invention provides a cell holder for use in the cryopreservation of an organic cell said holder including retaining means to retain the cell whilst allowing fluid to pass from the holder.

Preferably, said retaining means includes a filter.

Preferably, the cell holder includes sidewalls thereby forming a cup-shaped holding vessel defining an open top inlet.

Preferably, said sidewalls include filtration means.

Preferably, said filter includes a mesh, membrane, fibrous material or a perforated section.

Preferably, the cell holder includes an elongate handle for manipulating the cell holder.

In a third aspect the invention provides an organic cell cryopreservation frame for securing a cell holder, said cell holder according to the second aspect, said frame having:
a cell holder receiving portion for receiving said cell holder:
an engagement formation for releasably engaging said cell holder thereby aligning said holder in said predetermined orientation; and
a drainage path for directing fluid draining from said cell holder to a drainage outlet.

Preferably the frame includes an array of cell holder receiving portions and corresponding engagement formations for receiving a plurality of cell holders.

In a fourth aspect the invention provides an organic cell cryopreservation treatment station for treating an organic cell secured in an organic cell holder, said cell holder according to the second aspect, said treatment station including:
securing means for securing said cell holder in a predetermined position
a drain for receiving treatment fluid draining from said cell holder; and
temperature control means for controlling the temperature of said cell holder and cell.

Preferably, said securing means includes a frame for securing said cell holder in a predetermined orientation, said frame having:
a cell holder receiving portion for receiving said cell holder;
an engagement formation for releasably engaging said cell holder thereby aligning said holder in said predetermined orientation;
a drainage path for directing fluid draining from said cell holder to a drainage outlet; and
docking means for engaging corresponding docking means on the treatment station thereby aligning said frame into a predetermined orientation with said station.

In a fifth aspect the invention provides an organic cell cryopreservation treatment station according to the fourth aspect, wherein said treatment station is a washing station for washing said cell, said washing station including:
a drain for receiving treatment fluid draining from said cell holder; and
temperature control means for controlling the temperature of said cell holder and cell.

In a sixth aspect the invention provides an organic cell cryopreservation treatment station according to the fourth aspect, wherein said treatment station is a cooling station for cooling said cell, said cooling station including cooling means for cooling said cells to a cryopreservation temperature for cryopreservation.

In another aspect, the invention provides an organic cell cryopreservation apparatus for use in the cryopreservation of an organic cell said apparatus including:
a cell holder having retaining means to retain the organic cell whilst allowing for fluid to pass from the cell holder;
securing means for securing said cell holder in a predetermined orientation;
a treatment station for washing said oocytes, said treatment station including:
temperature control means; and
docking means for engaging corresponding docking means on the securing means thereby aligning said securing means into a predetermined orientation with said station.

Preferably, said apparatus further including a cooling station for cooling of said cells to a cryopreservation temperature.

Preferably, said cooling station includes liquid nitrogen cooled block.

BRIEF DESCRIPTION OF THE DRAWINGS

Preferred embodiments of the invention will now be described, by way of example only, with reference to the accompanying drawings in which:—

FIG. 1a is a perspective view of a cell holder according to the invention;

FIG. 1b is a perspective view of the cell holder shown in FIG. 1a;

FIG. 1c is a detailed part perspective view of a cell holding vessel of the cell holder shown in FIG. 1a;

FIGS. 1d and 1e are detailed part perspective views of alternative cell holders according to the invention;

FIG. 1f is a perspective view of a storing straw according to the invention;

FIG. 2a is a perspective view of a securing tray according to the invention;

FIG. 2b is a detailed part top perspective view of a cell holder located in the securing tray shown in FIG. 2a;

FIG. 2c is a detailed part bottom perspective view of a cell holder in the securing tray shown in FIG. 2a;

FIG. 2d is a detailed part top perspective view of a cell holder in the securing tray shown in FIG. 2a;

FIG. 3b is an exploded perspective view of the cover for the securing tray shown in FIG. 3a and the securing tray shown in FIG. 2a;

FIG. 3c is an exploded perspective view of the cover for the securing tray shown in FIG. 3a and the securing tray shown in FIG. 2a;

FIG. 4a is a perspective view of the cover for the securing tray shown in FIG. 3a mounted on the securing tray shown in FIG. 2a;

FIG. 4b is an underside perspective view of the cover for the securing tray shown in FIG. 3a mounted on the securing tray shown in FIG. 2a;

FIG. 4c is a perspective view of a washing station according to the invention;

FIG. 5a is a detailed part perspective view of FIG. 4a;

FIG. 5b is a detailed cross-sectional perspective view of the washing station shown in FIG. 4c and the tray and cover assembly shown in FIG. 4a;

FIG. 6a is an exploded perspective view of the tray and cover assembly shown in FIG. 4a and a cooling station in accordance with the invention;

FIG. 6b is a perspective view of the tray and cover assembly shown in FIG. 4a mounted on the cooling station shown in FIG. 6a;

FIG. 7a is a perspective view of the tray shown in FIG. 2a mounted on the cooling station shown in FIG. 6a;

FIG. 7b is a perspective view of the tray shown in FIG. 2a mounted on the cooling station shown in FIG. 6a with a cell holder removed;

FIG. 8a is a perspective view of the cell holder of FIG. 1a and straw of FIG. 1f;

FIG. 8b is a perspective view of the cell holder of FIG. 1a partially inserted into the straw of FIG. 1f; and FIG. 8c is a perspective view of the cell holder of FIG. 1a full inserted into the straw of FIG. 1f and ready for long term cold storage.

PREFERRED EMBODIMENTS OF THE INVENTION

Figure 3A:
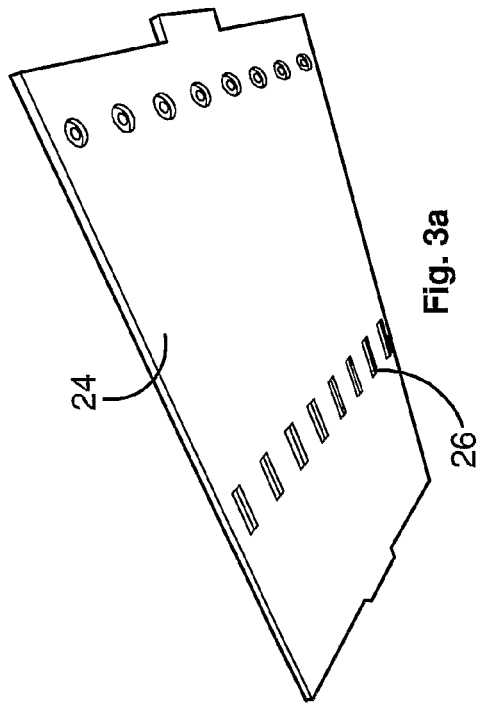
FIG. 3a is a perspective view of a cover for the securing tray shown in FIG. 2a, according to the invention.
Figure 3C:
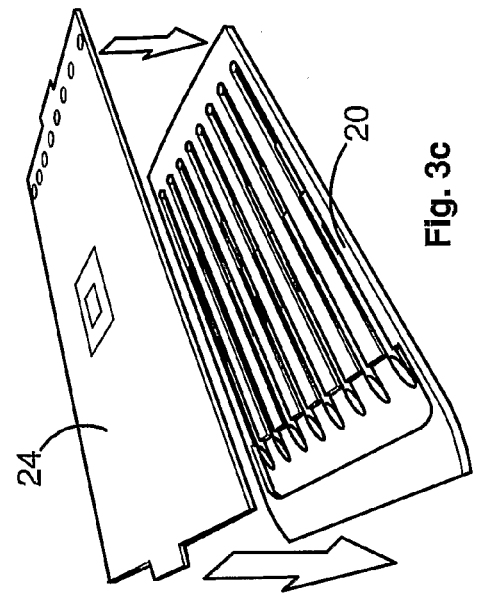
Figure 3B:
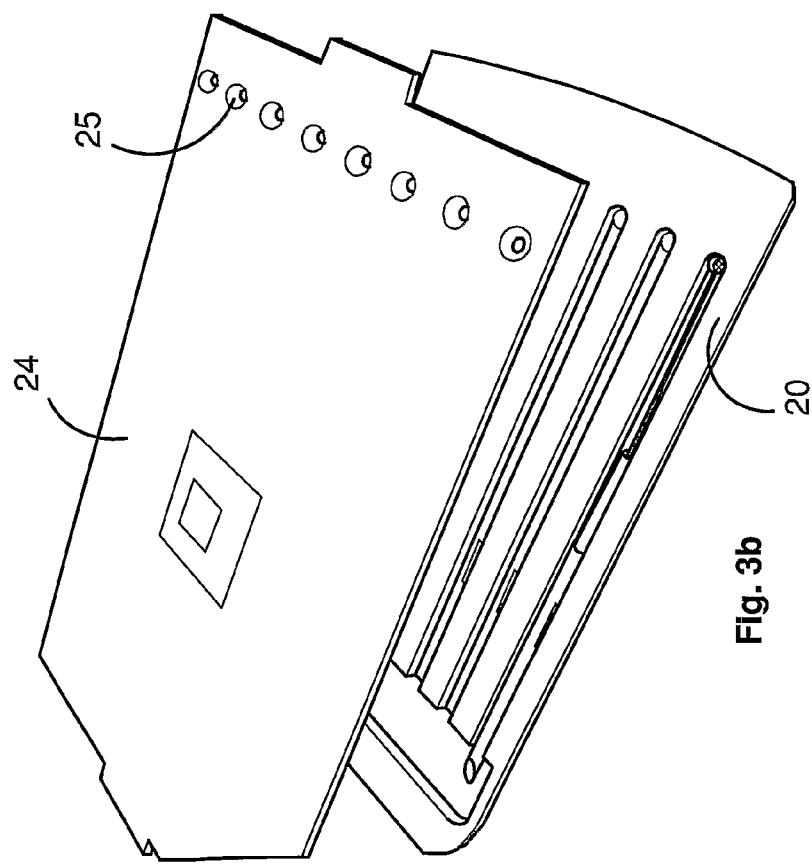

Referring to the drawings, the invention provides for a method and apparatus for the cryopreservation of oocyte, embryos and other cell types.

For the sake of simplicity, the preferred embodiment will be described with reference to oocyte cells however; the invention is not limited to the cryopreservation of oocytes and is intended to be equally applicable to other biological cells and tissues including individual cells such as stem cells, groups of cells such as embryos and tissue samples.

Additionally while the method and apparatus are described with reference to vitrification cryopreservation, it will be appreciate that it may be equally applied to other, methods of cryopreservation.

In its simplest form the method involves placing an oocyte cell in a cell holder, securing the cell holder in a treatment station, applying a treatment solution to said cell by washing the cell with the solution, and rapidly cooling the cell holder and cell to a predetermined cryopreservation temperature for cryopreservation of the cell. Preferably the cell is cooled at a high rate sufficient to permit solidification of the cell and any surrounding treatment solution to occur. More preferably, solidification includes the substantial vitrification of the cell and surrounding fluid. The cell is then maintained at or below a predetermined storage temperature for storage.

The invention includes multiple components designed to function together, enabling simple, safe and hygienic handling of the delicate cell. The method and apparatus also lends itself to multiplexing so that an individual technician may process more than one cell holder and oocyte cell simultaneously.

Referring to FIG. 1a the cell holder 1 includes retaining means to retain the organic cell whilst allowing for fluid to pass over the cell and through the cell holder. The retaining means includes a filter 2 to provide a physical barrier to the cell whilst allowing passage of a treatment solution. The filter can be seen in FIG. 1c which provides a close up view of the holder.

In this embodiment the holder also includes sidewalls 3, defining a 'cup-shaped' holding vessel 4 having an open top inlet 5. In this way, in the embodiment shown in FIG. 1c, the filter 2 forms the bottom surface of the vessel. In other embodiments however, the filter may form any portion of the vessel including the bottom and/or sidewalls. The filter 2 may be a mesh, membrane, fibrous material, perforated material or otherwise porous material which allows passage of liquids but which retains the oocyte within the vessel.

A further embodiment of vessel having converging sidewalls 6 is shown in detailed view FIG. 1d. The converging sidewalls reduce the likelihood of the cell being washed out of the vessel through the open top. In this view an embryo 7 is also shown. A further embodiment of the vessel holder is shown in FIG. 1e. In this embodiment, the sidewalls include cut outs.

In a further embodiment not shown in the Figures the vessel may include a removable cover. The cover may include a further filter material over a fluid inlet to allow passage of fluid into the cell holder whilst preventing the cell from escaping. Thus the cell is secured in a holding chamber. The filter on the cover may be of any filter material as previously described.

All of the embodiments shown in the Figures include an elongate handle 8 attached to the cell holder 1 to enable it and oocyte cell to be manually moved without direct contact from the operator. The handle also provides a convenient labelling area 9 for labelling and identification.

In this embodiment, the vessel is designed to fit into an elongate tubular sheath or straw 10 as shown in FIG. 1f. The straw 10 is open at one end 11 and sealed at the other 12. A circumferential ridge 13 on the handle of the cell holder 1 engages and seals with the inner bore 14 of the tubular straw 10 thereby sealing the oocyte within the straw once the freezing process is complete.

In alternative embodiments not shown in the drawings, the handle is selectively detachable. In further embodiments the handle is a separate tool designed to selectively engage and grip the cell holder so it can be moved as required. The tool may be in the form of a pincer type tool or include a simple fixed yoke or engagement formation to generally encircle and engage the cell holder. In such embodiments, the cell holder may include an engagement portion, formation or tab designed to releasably engage with the handle or tool.

In still further embodiments, the cell holder includes multiple holding vessels 4 joined together to provide for treatment and cryopreservation of multiple cells. The vessels, otherwise similar to any one or more of those described above, may be positioned at a predetermined spacing from one another in order to engage with other components, as will be appreciated from the description below. Alternatively, each cell holder may include linking formations to allow for multiple cell holders to be linked together, in effect forming a multiple vessel cell holder. This way cell holders can be quickly and easily joined together in the lab to provide for as many holding vessels as required. Preferably, the linking formations are configured to position the cell holders in a predetermined spacing.

The invention further includes a securing frame, for securing the cell holder. The frame is shown in FIG. 2a and in this embodiment is in the form of a tray 20. The tray includes an engagement formation 21 and a cell holder-receiving portion 22, each shown in detail FIGS. 2b and 2d, respectively. As will be appreciated with reference to the figures, in this embodiment the engagement formation 21 includes a shallow elongate locating groove for receiving and positively locating the handle 8 of the cell holder 1. In this way, the complementary shape and configuration of the cell holder handle 8 and the corresponding groove on the frame, bias the cell holder into a particular orientation and position with respect to the frame 20.

In position, as shown in the detailed upper view FIGS. 2b and 2d and lower view FIG. 2c, the cell holder is positioned within or over the receiving portion 22 of the frame 20. In this embodiment, as can clearly be seen in FIG. 2a, the receiving portion 22 includes an aperture in the tray so that the cell holder is accessible from above and the bottom of the cell holder is clear or protruding from the tray bottom.

The tray 20 may include a plurality of grooves for receiving a plurality of cell holders in an array. The tray illustrated in the figures has grooves for eight cell holders. However, it will be appreciated that a tray may accommodate more or fewer than eight cell holders.

In the alternative configuration where the cell holder does not include a handle, the engagement formation 21 on the tray 20 may include projections which engage the outer sidewall of the cell holder. In still further embodiments, the cell holder includes corresponding engagement formations to engage the engagement formations on the tray. Returning to the figures, the invention also includes securing means for locking the cell holders into the tray. In some embodiments, the cell holder and tray may include snap locking securing formations 23 to individually lock each cell holder directly to the tray. Such securing formation can be seen with reference to FIG. 2b and engage the cell holder handle 3.

In this embodiment, the securing means also includes a tray cover 24 to jointly hold the cell holders within the locating grooves 21 on the tray 20 thereby preventing their extraction and any relative movement within the tray. The cover 24 includes releasable locking means for locking to corresponding releasable locking means on the tray thereby securing the cover to the tray. The cover also includes a funnel formation and aperture 25. The funnel formation and aperture are configured such that when the cover is locked to the tray, the funnel and aperture are aligned with the open top of the cell holder. The function of the funnel will be detailed later. The cover may also include location formations 26 to engage and secure the cell holder handle. These location formations can be seen in the underside view of the cover in FIG. 3a.

It will be appreciated that locked into the tray, a plurality of cell holders may be safely and easily moved by an individual technician or by a mechanical manipulating device, automated robot or the like. In addition, because the relative position of the cell holders and tray are set, the tray can be used as a guide for aligning the array of cell holders for treatment at a treatment station.

In this regard the invention includes at least one treatment station to which the tray can be selectively docked and various operations performed. The station is configured for receiving the tray and includes docking formations for docking with corresponding docking formations on the tray.

A first treatment station is a washing station 30 shown in FIG. 4c. The washing station includes a drain 31 for capturing waste fluid and temperature control means 32. At this station the cells are held at a predetermined temperature by the temperature control means and washed with treatment solution.

A second treatment station is a cooling station 40, shown in FIGS. 6a and 6b where the cells and cell holders are cooled to below a cryopreservation temperature. Specific cooling properties of the cooling station will depend on the intended method of cryopreservation whether by slower rate freezing or rapid vitrification. The cooling station 41 includes a cooling block or similar device held at a very low temperature by liquid nitrogen.

In this embodiment the treatment and cooling stations are at distinct locations and the tray transferred between. However it is also possible that the tray is held at a fixed point and the stations are moved to align with the tray as required.

In use, an oocyte to be cryopreserved is placed into the holding vessel 4 of a cell holder 1 as shown in FIG. 1a. The cell holder 1 itself is generally pre-labelled with identification details regarding the cell and/or donor/s. The holder 1 is then placed into securing tray 20 so that the cell holder handle lies in the corresponding groove and the holder vessel is located in or above the receiving aperture 22. This can be seen in FIG. 2c where the base of the cell holder protrudes below the bottom surface of the tray. FIG. 2b shows the cell holder handle engaged in the locating groove and secured with snap locking securing formations 23. In the embodiment depicted, eight such cell holders are placed in the tray in an array of respective locating grooves.

With the cell holders in place, the tray cover is aligned with and locked onto the tray. In position, the funnel formations and apertures on the tray cover align with the open top of the cell holding vessels.

The tray is then transferred to the first treatment station, the washing station 30. Corresponding docking formations on the tray and washing station position the tray so that the vessel holders located are above the drain, adjacent the heating block 32. This can be seen in FIG. 5b where the cover 24 and funnel are positioned above the open top of the holding vessel, which is over the drain 31 of the washing station.

As seen in FIG. 5a fluid dispensing pipette 50 is positioned above the funnel formation to dispense a predetermined measure of treatment solution into each funnel aperture. The fluid flows down through the funnel, out the funnel aperture and into the holder vessel passing over and washing the oocyte cell. Excess fluid drains from the vessel through the filter 2 and passes into the drain.

The flow rate of fluid from the pipette and the proportions of the funnel are carefully chosen so that the treatment fluid delicately flows into the vessel. If the fluid flow rate is too high the fluid can damage the cells and/or overflow the vessel and possibly dislodge the cells. As a preventative measure, in some embodiments, an additional filtration membrane may be placed over the open top inlet 5 to retain the cell within the vessel.

Furthermore, in order to encourage flow of the treatment solution through the filter, the drain 31 is held at a negative pressure. In this regard the treatment station also includes vacuum means to apply a gentle negative pressure to the drain. A vacuum pump and corresponding control electronics are positioned within a cavity 33 of the washing station.

It also is critical during this process to maintain the oocyte cell at the correct temperature. To this end, the treatment fluid is held at a predetermined temperature in the pipette and the heating block 32 maintains the temperature of the cells at a predetermined level.

The cell may be treated with a sequence of different treatment solutions as required. The same pipette may be used for each solution or if the solutions are incompatible, a different pipette may be used for each solution. The last treatment solution to be applied is a vitrification fluid, which is vitrified along with the cell during the cooling and solidification.

In addition, it is intended that the array of oocytes in their respective holders located in the tray are all treated simultaneously. Accordingly a multi-headed pipette 50 as shown in FIG. 5a is used to dispense the treatment solution to each cell holder at the same time. Furthermore, the system also lends itself to automation or semi-automation. Since the position of the cell holders is dictated by the position of the tray, the entire washing procedure can be multiplexed and automated.

As such an automated system allows precise control over the delivery of the treatment solution, the temperature of the fluid and cell, which hitherto were difficult to achieve in a manual system.

Once the oocytes have been treated, the tray is removed from the washing station and transferred without delay to the cooling station 40. As with the washing station, the cooling station includes docking formations that engage corresponding docking formation on the tray 20. In position, the cell holder vessels are aligned with the cooling station vitrification block 41. The vitrification block is cooled with liquid nitrogen such that cooling occurs within moments of contact at a rate sufficient to transform the cell and any surrounding vitrification fluid into a vitrified state. The block may be immersed in or contain the liquid nitrogen so that it is at a similar temperature to the liquid nitrogen.

Figures 7A, 7B:
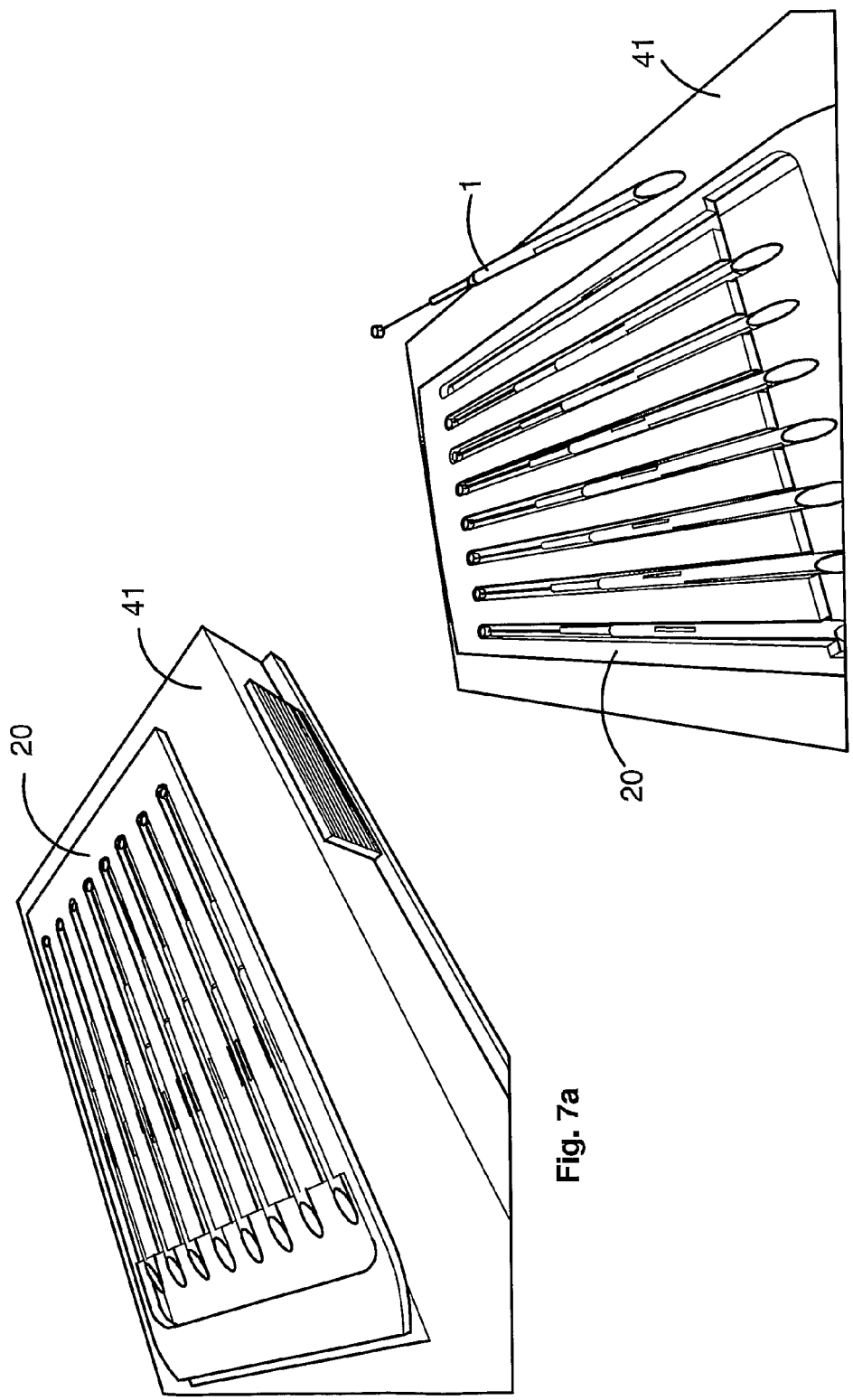

While vitrification of the oocytes or cells occurs very quickly, the cell holders are kept in position in the cooling station for a predetermined period to ensure the cells are cooled to a suitably low temperature. With the tray mounted to the cooling station, FIG. 7a, the tray cover is removed and each cell holder containing a vitrified oocyte is removed from the tray, FIG. 7b, and inserted into a pre-cooled straw 10, FIG. 8b, or other suitable holding device. In this form the oocyte is securely contained, FIG. 8c, and can be placed into long-term cold storage.

Again, the process of removal from the tray, insertion into a straw and then storage is automated. In alternative embodiments it can be performed manually.

Advantageously, it will be appreciated that the system allows the preparation of the embryo/oocyte for cryopreservation to be carefully controlled. In addition, the proposed system allows for the preparation and vitrification of multiple embryos/oocytes simultaneously.

The process allows for the treatment process to be uniformly controlled removing variances of the washing and vitrification process. In addition, the invention provides for less manipulation of the cells because they remain generally stationary in the cell holder through out the treatment and vitrification process. In these and other respects, the invention represents a practical and commercially significant improvement over the prior art.

Although the invention has been described with reference to specific examples, it will be appreciated by those skilled in the art that the invention may be embodied in many other forms.

The invention claimed is:

1. A method for the cryopreservation of a biological cell, said method comprising the steps of:
    providing a biological cell in a cell holder comprising sidewalls thereby forming a cup-shaped holding vessel and defining an open inlet to hold the biological cell for cryopreservation of the biological cell, wherein said cell holding vessel includes filtration means formed at a lower surface of said vessel;
    securing the cell holder containing the biological cell at a treatment station in a cell holder frame including a plurality of locating formations and secured to the treatment station, and providing each locating formation for securing a respective said cell holder, to thereby allow a plurality of corresponding cell holders to be secured to the frame in an array;
    subsequent to the securing, automatically applying a cryopreservation treatment solution to the biological cell at the treatment station;
    subsequent to the applying, and without delay, cooling said cell holder and biological cell to a predetermined cryopreservation temperature at a cooling station, such that said biological cell is cooled at a cooling rate sufficient to promote vitrification of the biological cell and surrounding cryopreservation treatment solution; and
    maintaining the biological cell at or below a storage temperature at the cooling station, wherein said step of applying a cryopreservation treatment solution includes the step of retaining said biological cell in said cell holder and allowing said cryopreservation treatment solution to flow through said cell holder.

2. A method according to claim 1 wherein said step of applying a cryopreservation treatment solution includes sequentially applying first and second treatment solutions to said biological cell.

3. A method according to claim 1 wherein applying the cryopreservation treatment solution includes sequentially applying a plurality of treatment solutions to said biological cell.

4. A method according to claim 1 wherein said cryopreservation treatment solution is a vitrification solution.

5. A method according to claim 1 wherein a plurality of said cell holders are secured in an array at the treatment station, simultaneously.

6. A method according to claim 1 wherein said biological cell includes one of:
    an oocyte cell,
    a stem cell,
    an embryo, and
    a tissue sample.

* * * * *